United States Patent [19]

Kuykendall et al.

[11] Patent Number: 5,021,076

[45] Date of Patent: Jun. 4, 1991

[54] **ENHANCEMENT OF NITROGEN FIXATION WITH *BRADYRHIZOBIUM JAPONICUM* MUTANTS**

[75] Inventors: Larry D. Kuykendall, Columbia, Md.; William J. Hunter, Fort Collins, Colo.

[73] Assignee: The United States of America as represented by the Secretary of Agriculture, Washington, D.C.

[21] Appl. No.: 325,184

[22] Filed: Mar. 17, 1989

[51] Int. Cl.$^5$ ...................... C12P 01/04; C12N 01/20; C05F 11/08
[52] U.S. Cl. ........................................... 71/7; 435/41; 435/252.2; 435/878
[58] Field of Search ...................... 435/252.2, 878, 41; 424/93

[56] References Cited

U.S. PATENT DOCUMENTS 4,711,656  12/1987  Kaneshiro ................................. 71/7

OTHER PUBLICATIONS

S. E. Wells and L. D. Kuykendall, "Tryptophan Auxotrophs of *Rhizobium japonicum*", J. Bacteriol. 156(3): 1356–1358 (1983).

W. J. Hunter, "Influence of 5-Methyltryptophan-Resistant *Bradyrhizobium japonicum* on Soybean Root Nodule Indole-3-Acetic Acid Content", Appl. Environ. Microbiol. 53(5): 1051–1055 (1987).

T. Kaneshiro and W. F. Kwolek, "Stimulated Nodulation of Soybeans by *Rhizobium japonicum* Mutant (B-14075) that Catabolizes the Conversion of Tryptophan to Indol-3yl-Acetic Acid", Plant Sci. 42: 141–146 (1985).

W. J. Hunter, "Increased Symbiotic Nodulation and Nitrogen Fixation by a 5-Methyltryptophan Resistant *Bradyrhizobium japonicum*", Abstract 861, Suppl. Plant Physiol. 86(4): 144 (Apr. 1988).

Kuykendall, L. D., "Isolation and Identification of Genetically Marked Strains of Nitrogen-Fixing Microsymbionts of Soybeans", Symbiotic Nitrogen Fixation Technology, N.Y., N.Y., Marcel Dekker Inc., 1987.

*Primary Examiner*—Douglas W. Robinson
*Assistant Examiner*—Marian C. Knode
*Attorney, Agent, or Firm*—M. Howard Silverstein; Curtis P. Ribando; John D. Fado

[57] ABSTRACT

A prototrophic revertant of a *Bradyrhizobium japonicum* tryptophan auxotroph was isolated and found to fix more nitrogen symbiotically than wild-type bacteria. The increase in nitrogen fixation is due to an increase in nodule mass because of an increase in nodule number. The physiological basis for this improved symbiosis appears to be an alteration of the tryptophan biosynthetic pathway.

7 Claims, No Drawings

ENHANCEMENT OF NITROGEN FIXATION WITH *BRADYRHIZOBIUM JAPONICUM* MUTANTS

BACKGROUND OF THE INVENTION

1. Field of the Invention

This invention relates to new mutant strains of *Bradyrhizobium japonicum* which in symbiotic combination with leguminous plants increase the nitrogen-fixing capability of the plant. This invention also relates to the commercial practice of inoculating soybeans and other legume seedlings with bacteria to increase effective nodulation and growth of leguminous crops.

2. Description of the Prior Art

The fixation of atmospheric nitrogen associated with specific legumes is the result of a highly specific symbiotic relationship with rhizobial bacteria. These indigenous bacteria dwell in the soil and are responsible for the formation of nodules in the roots of leguminous plants as sites for the nitrogen fixation. Currently, these rhizobia are classified by growth rate in free-living cultures, with the fast-growing organisms being designated as Rhizobium and the slow-growing organisms as Bradyrhizobium. Many of the rhizobial strains are not only host-specific but also differ with respect to capacity for effective symbiosis. Those strains which are able to infect a plurality of host plants across species or genus lines are said to be "cross-nodulating." Commercial inocula generally consist of a mixture of rhizobial strains to insure the widest potential for effective symbiosis within the appropriate crop.

In the art of soybean cultivation, unspecified strains of *B. japonicum* have become recognized as standard inoculants for initiating nodulation and nitrogen fixation.

The symbiotic properties of *Bradyrhizobium japonicum* mutants with altered tryptophan biosynthetic pathways have been investigated. Wells and Kuykendall [*J. Bacteriol.* 156: 1356–1358 (1983)] isolated a series of tryptophan-requiring mutants of *B. japonicum* I-110ARS. These mutants fell into five classes according to their enzyme deficiencies. Only mutants that were defective in tryptophan synthetase, the last step of the tryptophan biosynthetic pathway, were capable of forming nodules. Other mutants, with defects earlier in the pathway, did not nodulate as auxotrophs but did as prototrophic revertants. Also, *B. japonicum* I-110 mutants that are resistant to 5-methyltryptophan and that constitutively overproduce tryptophan and tryptophan pathway products have been isolated and studied [Hunter, *Appl. Environ. Microbiol.* 53: 1051–1055 (1987)]. Generally, these bacteria were poor nodulators and poor nitrogen fixers.

Kaneshiro and Kwolek [*Plant Sci.* 42: 141–146 (1985)] reported that trypotophan catabolic variants of a Bradyrhizobium sp. (soybean) strain L-259 had improved symbiotic properties. It is characteristic of these catabolic mutants, when grown in the presence of tryptophan, to degrade tryptophan rapidly, to accumulate large amounts of indole compounds, and to produce a tan pigment.

SUMMARY OF THE INVENTION

We have now surprisingly discovered a new symbiotic prototrophic revertant of a non-nodulating tryptophan auxotroph (TA-11) of *Bradyrhizobium japonicum*. In symbiotic relationship with leguminous plants, this new strain produces significantly more nitrogen per plant as compared to plants inoculated with wild-type bacteria.

In accordance with this discovery, it is an object of the invention to provide improved bacterial strains for inoculating leguminous crops to increase symbiotic fixation of atmospheric nitrogen.

A further object of the invention is to enhance the potential of soybeans and other leguminous plants for symbiotic fixation of atmospheric nitrogen.

More particularly, it is an object of the invention to employ a new strain of *Bradyrhizobium japonicum* designated TA-11 Nod+, NRRC B-18466, for inocula in conjunction with leguminous crops.

Other objects and advantages of this invention will become readily apparent from the ensuing detailed description.

DETAILED DESCRIPTION OF THE INVENTION

Wells and Kuykendall [supra] described a series of tryptophan-requiring mutants of *B. japonicum* that were isolated from strain I-110ARS. One class of mutant was deficient in indole glycerol phosphate synthase and was found to be incapable of forming nodules when inoculated into legumes. However, bacteria that have regained their ability to produce tryptophan can nodulate.

We have now isolated prototrophic revertants of strain TA-11. Parent TA-11 has been deposited under the conditions of the Budapest Treaty with the United States Department of Agriculture in the Agricultural Research Service Culture Collection (NRRL) at the Northern Regional Research Center in Peoria, Ill. 61604, and has been assigned accession number NRRL B-18465. The new strains are capable of acting in a symbiotic manner with legumes to increase nitrogen fixation in the plant.

The new revertant strain TA-11 Nod+ is representative of the prototrophic revertant strains derived from strain TA-11. This strain has been deposited under the conditions of the Budapest Treaty with the United States Department of Agriculture in the Agricultural Research Service Culture Collection (NRRL) at the Northern Regional Research Center, Peoria, Ill. 61604. Its accession number is NRRL B-18466. The general procedure for selection of revertant strains is given in Example 2.

Strain TA-11 Nod+ is a revertant that phenotypically resembles the wild-type progenitor strain I-110ARS in that it no longer requires tryptophan for growth as does strain TA-11, but differs in that it exhibits superior nitrogen fixation and other symbiotic properties. Greenhouse studies demonstrated that plants receiving the TA-11 Nod+ revertant had enhanced nitrogen fixation as evidenced by better color, higher dry weights, and larger nodule mass than did plants inoculated with wild-type bacteria. Subsequent experiments showed that plants inoculated with TA-11 Nod+ were 33% larger and contained 52% more nitrogen and 34% more carbon than plants inoculated with the wild-type progenitor strain I-110ARS (Table I). Also, plants treated with the revertant had 56% more nodules and 41% more nodule mass than did plants inoculated with the wild-type *B. japonicum* strain I-110ARS. Average nodule size and amount of nitrogen fixed per gram of nodule were about the same with both inocula (Table II). The improvement in nitrogen fixation observed with the TA-11 Nod+ revertants is correlated with an increase in nodule mass and an increased number of nodules per plant.

Virtually all members of the legume family are candidate benefactors of the method of the invention. Without limitation thereto, plants which can be advantageously treated with an appropriate mutant rhizobia include soybeans, cowpeas, lupines, mungbeans, and other legumes such as alfalfa and clover. Of principal interest are crop species, particularly those which are routinely inoculated with specific rhizobial strains for the purpose of enhancing nodulation, nitrogen-fixation, or the general growth properties of the plant.

Inoculation of the leguminous plants with the revertant strains may be conducted by conventional techniques as known in the art. Suitable inocula include culture broths and agronomically acceptable carrier media containing cells of the organism. The inoculum may be applied to the seeds prior to planting or to the roots of seedlings after germination. Alternatively, the organism can be established in the locus of the plant, such as by incorporation into the soil before or after planting. In this regard, it would be advantageous to apply the inoculum in combination with other agronomic chemicals or adjuvants such as fertilizers and soil conditioners. The inoculum may comprise either a monoculture of a revertant strain, a mixed culture of a revertant strain, or even a revertant strain in combination with other rhizobia. It is also within the ambit of the matic conditions is another factor influencing a symbiosis and requiring consideration as necessary.

Without being bound to any particular theory of operation, it is believed that the strains I-110 ARS, TA-11, and TA-11Nod+ revertants are different in their tryptophan biosynthesis. This conclusion is supported by the following evidence. First, the TA-11 auxotroph, from which the TA-11 Nod+ revertants can be repeatedly and reproducibly obtained using the procedure outlined in Example 2, is a well-defined trylophan-requiring mutant known to be defective in a single enzyme of the tryptophan trosynthetic pathway [Wells and Kuykendall, supra]. TA-11 Nod+ revertants are obtained from strain TA-11 in a single step selection, it is therefore clear that no more than a single mutation is involved in the reversion to prototrophy. The change that did occur involves the tryptophan biosynthetic pathway as it corrects for the enzyme deficiency that existed in the auxotroph. Second, tryptophan in large amounts inhibits the growth of bradyrhizobia, and the wild-type progenitor strain I-110ARS is more sensitive to the effects of tryptophan than is the TA-11 Nod+ strain (Table III). This higher resistance to tryptophan by the TA-11 Nod+ strain serves to clearly distinguish it from strain I-110ARS and is due to an alteration in how the TA-11Nod+ cells handle tryptophan biosynthesis.

Kaneshiro [U.S. Pat. No. 4,711,656 (1987)] and Kaneshiro and Kwolek [supra] have reported that the tan 4b and 20d mutants of *B. japonicum* L-259 that exhibit

TABLE I

Effect of Inocula on Plant Dry Weight and on Carbon and Nitrogen Content

Plants were grown in greenhouse hydroponic pots and analyzed as described in Example 5. Values are an average of 6 to 10 replicates ± SE.

| Inoculum | Dry Wt. (g) | | Shoot (g) | | Root (g) | |
|---|---|---|---|---|---|---|
| | Shoot | Root | C | N | C | N |
| None | 1.3 ± 0.1 | 0.8 ± 0.1 | 0.408 ± 0.044 | 0.015 ± 0.001 | 0.277 ± 0.029 | 0.012 ± 0.001 |
| Wild-Type | 5.2 ± 0.6 | 1.2 ± 0.1 | 2.11 ± 0.22 | 0.169 ± 0.016 | 0.433 ± 0.033 | 0.023 ± 0.002 |
| TA-11 Nod+ | 6.8 ± 0.8 | 1.7 ± 0.2 | 2.80 ± 0.33 | 0.242 ± 0.032 | 0.632 ± 0.065 | 0.035 ± 0.004 |

TABLE II

Effect of Inoculum on Nodule Number, Mass, Weight, and Activity

Conditions were as described in Table I. Mass is wet weight of nodules per plant. Average weight is the average wet weight of an individual nodule. Activity provides an estimation of the amount of nitrogen fixed per gram of nodule and was derived by subtracting the N content of the uninoculated control plants from the N content of the treatment plants and dividing by nodule mass.

| | Nodule | | | |
|---|---|---|---|---|
| Inoculum | Number | Mass (g) | Ave. Wt. (g) | Activity |
| Wild-Type | 134 ± 16 | 2.9 ± 0.2 | 0.023 | 0.043 |
| TA-11 Nod+ | 209 ± 21 | 4.1 ± 0.5 | 0.020 | 0.044 | invention to employ revertant strains derived from rhizobial strains that can cross-nodulate between wild hosts and cultivated crops.

It is of course appreciated by the skilled artisan that dominance of competitive species is a factor in both infectivity and nodulation, and special precautions may therefore be necessary to insure infection of specific plants. Competition may arise from other indigenous organisms in the natural microflora of the soil. Compatibility of a particular rhizobial strain with soil and clienhanced nodulation and nitrogen fixation do so as a result of enhanced tryptophan catabolism.

TABLE III

Effect of Tryptophan on Colony Size

Colonies were grown at 30° C. for 9 days on A1E media supplemented with tryptophan as indicated. Measurements were made at 40× using a microscope equipped with an eyepiece micrometer. Values are the mean of 10 to 30 measurements ± SD.

| Tryptophan Addition (mM) | Colony Size | |
|---|---|---|
| | Wild-Type (mm) | TA-11 Nod+ (mm) |
| None | 0.93 ± 0.02 | 0.94 ± 0.03 |
| 10 | 0.80 ± 0.01 | 0.77 ± 0.01 |
| 20 | 0.60 ± 0.01 | 0.66 ± 0.01 |
| 30 | 0.38 ± 0.02 | 0.47 ± 0.01 |
| 40 | 0.13 ± 0.01 | 0.27 ± 0.0 |

The, following studies clearly demonstrate that the TA-11 Nod+ strain does not exhibit enhanced tryptophan catabolism. Therefore, it is evident that the TA-11 Nod+ bacteria are different and distinguishable from the tan mutants of *B. japonicum* L-259.

Tryptophan loss and pigment production by bradyrhizobia grown in media supplemented with tryptophan were studied for the TA-11 Nod+ mutant and wild-type *B. japonicum* I-110ARS, as well as the tan 4b and tan 20d mutants of Kaneshiro [supra] and wild-type *B. japonicum* L-259. The TA-11 Nod+ strain closely resembles wild-type I-110ARS; both removed about the same amount of tryptophan from the growth media and both accumulated only trace amounts of pigment (Table IV). This evidence shows that the TA-11 Nod+ strain is not a strain with enhanced tryptophan catabolism. In contrast, Kaneshiro's tan mutants rapidly removed large amounts of tryptophan from the medium and rapidly produced large amounts of pigment [Table IV; Kaneshiro et al., *Curr. Microbio.* 8: 301–306 (1983); Kaneshiro, supra (1987); Kaneshiro and Nicholson, *Curr. Microbiol.* 18: 57–60 (1989)].

The accumulation of 3-indoleacetic, 3-indolelactic, and anthranilic acids in culture fluid was examined in the wild-type I-110ARS and TA-11 Nod+ strains. The tan mutants of L-259 are known to accumulate large amounts of IAA and ILA when grown on tryptophan-containing media, and they accumulate these compounds faster and in larger amounts than does their parent, L-259 [Kaneshiro et al., supra; Kaneshiro, supra (1987); Kaneshiro and Nicholson, supra].

IAA and anthranilic acid do not accumulate in either the TA-11 Nod+ or wild-type I-110ARS cultures. Levels of these compounds are the same as or lower than those present in the uninoculated control. ILA accumulated but only in small and approximately equal amounts in cultures of both strains.

TABLE IV

Tryptophan Disappearance and Pigment Production by Wild-Type and Mutant *B. Japonicum* I-110 and L-259

Fermentation flasks were incubated for 4 days at 30° C. and 130 rpm. Flasks contained 25 ml of A1E medium supplemented with 39 μmoles (0.3 g/l) of tryptophan. Growth is turbidity at 660 nm. Tryptophan loss is in μmoles per fermentation flask as determined by high-performance liquid chromatography as described in Example 6. For pigment production, culture fluid was centrifuged at 10,000 g for 20 min, and the supernatant fluid was monitored at 480 nm. All values are a mean of 3 replicates ± standard error.

| Strain | Growth ($mA_{660}$) | Tryptophan Loss (μmoles) | Pigment Produced ($mA_{480}$) |
|---|---|---|---|
| *B. japonicum* I-110 | | | |
| Wild-type I-110 | 887 ± 33 | 6 ± 0 | 9 ± 0 |
| TA-11 Nod+ | 890 ± 15 | 7 ± 1 | 8 ± 0 |
| *B. japonicum* L-259 | | | |
| Wild-type L-259 | 950 ± 26 | 6 ± 1 | 25 ± 7 |
| B-14075 (Tan 20d) | 880 ± 10 | 34 ± 1 | 531 ± 10 |
| B-14077 (Tan 4b) | 870 ± 42 | 34 ± 1 | 417 ± 56 |

These data demonstrate that the TA-11 Nod+ mutant resembles the wild-type strain I-110ARS with respect to these three important accumulation products. These data provide additional proof that the TA-11 Nod+ mutant is not a mutant with enhanced tryptophan catabolism, and serves to further differentiate the TA-11 Nod+ strain from Kaneshiro's tan mutants derived from L-259.

The following examples are intended only to further illustrate the invention and are not intended to limit the scope of the invention which is defined by the claims.

EXAMPLE 1

Bacterial Cultures

The wild-type *B. japonicum* strain I-110 ARS is a genetically marked sublime of substrain I-110 of USDA 110 and is resistant to azide, rifampin, and streptomycin [Kuykendall and Elkan, *Appl. Environ. Microbiol.* 32: 511–519 (1976); Kuykendall and Weber, *Appl. Environ. Microbiol.* 36: 915–919 (1978)]. Strain TA-11 Nod+ is a spontaneous prototrophic revertant of a tryptophan-requiring auxotroph. The auxotroph, strain TA-11, was derived from the wild-type I-110 ARS strain and is known to be deficient in a single enzyme of the tryptophan biosynthetic pathway, indole glycerol phosphate synthetase activity. Due to this enzyme deficiency, it requires tryptophan for growth [Wells and Kuykendall, supra]. Also, it is considered to be a non-nodulator as it does not form nodules from which auxotrophs can be isolated. The TA-11 auxotroph and TA-11 Nod+ prototrophic revertant have been deposited in the Agricultural Research Service Culture Collection (NRRL), Peoria, Ill. 61604, under the designations NRRL B-18465 and NRRL B-18466, respectively.

*B. japonicum* L-259 (USDA strain 26) and the mutant strains B-14075 and B-14077 (tan 4b) derived from L-259 were obtained from the Agricultural Research Service Culture Collection (NRRL), Peoria, Ill. 61604.

EXAMPLE 2

Isolation of Prototrophic Revertants from Strain TA-11

Eleven tryptophan-requiring mutants of *Bradyrhizobium japonicum* strain I-110 ARS were characterized by Wells and Kuykendall [supra] and were placed into five biochemical classes according to enzyme deficiencies. Only three of these mutants, those that are specifically defective in tryptophan synthetase, could nodulate soybean plants. The other mutant strains with defects earlier in the pathway, including the indole glycerol phosphate synthetase deficient strain TA-11, did not nodulate soybeans as auxotrophs. The Trp− mutant strain TA-11 forms only abortive nodules as an amino acid-requiring strain that is incapable of growth on minimal media.

Reversion frequencies. The various complete, selective, and minimal culture media for growth of *B. japonicum* strains were described by Kuykendall ["Isolation and Identification of Genetically Marked Strains of Nitrogen-Fixing Microsymbionts of Soybeans," in: *Practical Symbiotic Nitrogen Fixation Methodology* (New York, Marcel Dekker, Inc., 1987, G. H. Elkan, ed.). Strain TA-11 was grown in A1E medium supplemented with tryptophan at 100 μg/ml for 4 days at 30° C. on a rotary shaker (New Brunswick). Turbidity measurements, taken using a Klett-Summerson colorimeter (red filter), indicated a cell density of about $1.5 \times 10^9$ bacteria per milliliter by reference to a standard curve relating optical density in Klett units to cell count. Prototrophic revertants that are capable of forming normal nodules on soybean can be selected on minimal media. Mutants of strain TA-11 that have acquired independence from tryptophan as a requirement for growth occur at a frequency of about $2 \times 10^{-7}$, or in other words about 20 revertants are obtained on 10 such petri dish selections where a total of about one billion viable cells of TA-11 were plated. Alternatively, as is described below, prototrophic revertants that form more nodules per plant than does strain I-110 can be selected and obtained from normal-appearing nodules formed on Kent soybeans with strain TA-11 used as inoculum. The frequency of prototrophic reversion was quantified using the same broth cultures as were subsequently used for seed inoculations.

Selection of mutants. Using soybean plants, all plants were grown in half-strength, nitrogen-free nutrient solution [Norris, *Com. Bur. of Pastures and Field Crops Hurley Bershire Bul.* 47: 186–198 (1964)]. Soybean seeds were surface-sterilized in 0.1% acidified $HgCl_2$ [Vincent, "*A Manual for the Practical Study of Root-Nodule Bacteria,*" Blackwell Scientific Publications, Oxford (1970)]. Leonard jars [Leonard, *J. Bacteriol.* 45: 523–527 (1943)] were used as containers to grow plants. Five seeds per jar were inoculated, each with 1.0 ml of late log phase culture of strain TA-11 grown as described above. Plants were grown with a 16-hr day at 30° C. and 24° C. night. Cotyledons were removed at 8 days and seedlings were thinned to four per jar. After 5 weeks of growth, plant roots were excised at the first node. Nodules were carefully removed from the roots by hand and were surface-sterilized in freshly prepared 3% $H_2O_2$ solution for 1 hr. The nodules were then thoroughly washed with sterile water to remove the disinfectant. Nodules were crushed with a sterile glass rod and the contents streaked onto both minimal and tryptophan-supplemented media.

Prototrophic revertants derived from strain TA-11 were streaked on selective media containing the appropriate antibiotics (500 μg/ml rifampicin and 1 mg/ml streptomycin) to confirm their status as derivatives of the parent strain I-110 ARS.

EXAMPLE 3

Media and Culture Conditions

A HEPES (N-2-hydroxyethyl piperazine-N'-2 ethanesulfonic acid) and MES [2-(N-morpholino)ethanesulfonic acid] buffered nutrient solution [Cole and Elkan, *Antimicrob. Agents Chemother* 4: 248–253 (1973)] was supplemented with 0.1% (w/v) L-arabinose to make the AOE minimal nutrient medium, and with arabinose and 1 g per liter yeast extract to make the A1E medium [Kuykendall, supra]. Arabinose was filter sterilized and added to the autoclaved base medium. For solid media, 1.5% (w/v) agar was added. Incubations were at 30° C. and broths were shaken at 130 rpm. Unless otherwise indicated, the A1E medium was used for the growth and maintenance of all bacteria.

EXAMPLE 4

Greenhouse Nodulation and Nitrogen Fixation Studies

Soybean [*Glycine max* (L.) Merr. cv. Tracy M] seeds were treated with ethanol and sodium hypochlorite to eliminate viable rhizobia and bradyrhizobia from the surface of the seed. Seeds were placed in plates containing autoclaved 1.5% (w/v) agar in tap water and incubated in the dark at 30° C. for 4 days. On day 4, germinated seedlings were inoculated with wild-type or TA-11 Nod+ bacteria. Seedlings were incubated for 4 or 5 hr more and then transferred to hydroponic pots in the greenhouse. Two seedlings were placed in each pot, and each greenhouse pot contained 8 liters of one-fifth strength Hoaglands medium modified as indicated by replacing nitrate salts with chloride salts. The plants were first placed in a nutrient solution that contained 0.38 mM nitrate. After two weeks in the greenhouse, this nutrient solution was replaced with one that was nitrogen-free; plants were maintained on a nitrogen-free nutrient solution for the rest of the study. Plants received fresh solutions once in the second week, once in the third week, and three times in the fourth week of growth. Plants were harvested after 35 days in the greenhouse. Details of treatment of seeds and greenhouse conditions were as described by Hunter [*Physiol. Plant.* 60: 467–472 (1984)].

EXAMPLE 5

Plant Dry Weight and Carbon and Nitrogen Content

Plant samples were dried for 72 hr in a 65° C. forced air oven and ground to 200 mesh; approximately 20 mg of this material was analyzed for carbon and nitrogen content by automated combustion on a Carlo Erba NA-1500 analyzer [Starr et al., *J. Agric. Sci.* 103: 471–473 (1984)]. Each plant sample was analyzed three times, and the results were averaged.

EXAMPLE 6

Culture Fluid Tryptophan Analysis

Culture fluid was centrifuged at 10,000 g for 20 min to remove bacterial cells, and 20 μl of the resulting supernatant fluid was injected into an isocratic HPLC equipped with a 250×4.6 mm C-18 reverse phase column. The HPLC buffer was 50 mM acetic acid and 50 mM potassium phosphate at a pH of 4.5, mixed 1:1 (v/v) with methanol. The column effluent was monitored at 280 nm.

EXAMPLE 7

IAA, ILA, and Anthranilic Acid Analysis

Culture fluid was centrifuged at 10,000 g for 20 min, and a 15-ml sample of supernatant fluid was removed. The pH of this sample was adjusted to 2.5 with 1.2M HCl and the sample was extracted three times with 5 ml volumes of ethyl acetate. Ethyl acetate fractions were combined, and the solvent was evaporated under a stream of dry nitrogen gas. Dried samples were suspended in 200 μl of methanol, and 20 μl was injected into an HPLC equipped with a 250×4.6 mm C-18 column. Analysis was isocratic. Buffer was 8.5 mM (0.5%) acetic acid in 50% (v/v) methanol (Table V).

It is understood that the foregoing detailed description is given merely by way of illustration and that modifications and variations may be made therein without departing from the spirit and scope of the invention.

TABLE V

Accumulation of the tryptophan degradation products 3-indoleacetic acid (IAA), 3-indolelactic acid (ILA) and anthranilic acid in cultures of *B. japonicum* strains I-110 and TA-11 Nod+. Cultures were grown for 3 weeks at 30° C. in AOE media supplemented with 20 mM tryptophan. Products were measured with an HPLC equipped with a C-18 reverse phase column and UV and fluorescent detectors. Values are an average of 3 to 4 replicates ± SE unless otherwise indicated.

| Strain | Degradation Product (nmoles) | | |
|---|---|---|---|
| | IAA | ILA | Anthranilic |
| Uninoculated control | 0.25 ± 0.02 | 0.14 ± 0.08 | 0.63 ± 0.13[a] |
| Wild-Type I-110 | 0.32 ± 0.18 | 3.07 ± 0.60 | 0.17 ± 0.08 |
| TA-11 Nod+ | 0.26 ± 0.03 | 3.52 ± 0.26 | 0.09 ± 0.02 |

[a]Value is an average of 2 replicates.

We claim:

1. A stable prototrophic revertant of the non-nodulating TA-11 auxotroph NRRL B-18465 derived from wild-type *Bradyrhizobium japonicum* I-110 ARS, said revertant being capable of enhanced nodulation and nitrogen-fixation in leguminous plants as compared to said wild-type.

2. A stable prototrophic revertant of claim 1, wherein said revertant has all the identifying characteristics of TA-11 Nod+ having accession number NRRL B-18466.

3. A stable prototrophic revertant of claim 1 wherein said leguminous plant is a soybean plant.

4. A method for promoting nitrogen fixation by *Bradyrhizobium japonicum* in symbiotic combination with a leguminous plant comprising inoculating the plant or the locus of the plant roots with an effective amount of a stable prototrophic revertant of the non-nodulating TA-11 auxotroph NRRL B-18465 derived from wild-type *Bradyrhizobium japonicum* I-110 ARS, said revertant being capable of enhanced nodulation and nitrogen-fixation in leguminous plants as compared to said wild-type, and culturing the inoculated plant in an environment conducive to symbiotic nitrogen fixation.

5. The method of claim 4 wherein said leguminous plant is a soybean plant.

6. The method of claim 4 wherein said revertant has all the identifying characteristics of TA-11 Nod+ having accession number NRRL B-18466.

7. The method of claim 4 wherein said leguminous plant is a soybean plant.

* * * * *